(12) United States Patent
Tallent et al.

(10) Patent No.: US 8,844,820 B2
(45) Date of Patent: Sep. 30, 2014

(54) MULTI-DIRECTIONAL OPTICAL READER FOR A PATIENT SUPPORT

(75) Inventors: Dan R. Tallent, Hope, IN (US); Robert M. Zerhusen, Cincinnati, OH (US)

(73) Assignee: Hill-Rom Services, Inc., Batesville, IN (US)

( * ) Notice: Subject to any disclaimer, the term of this patent is extended or adjusted under 35 U.S.C. 154(b) by 371 days.

(21) Appl. No.: 13/216,341

(22) Filed: Aug. 24, 2011

(65) Prior Publication Data

US 2013/0048705 A1 Feb. 28, 2013

(51) Int. Cl.
| | |
|---|---|
| G06K 19/00 | (2006.01) |
| G06Q 10/08 | (2012.01) |
| G06Q 10/06 | (2012.01) |
| A61B 5/11 | (2006.01) |
| A61B 5/00 | (2006.01) |
| A61G 7/05 | (2006.01) |

(52) U.S. Cl.
CPC ............... *G06Q 10/06* (2013.01); *A61B 5/1113* (2013.01); *A61G 2203/20* (2013.01); *A61B 5/7495* (2013.01); *G06Q 10/087* (2013.01); *A61B 5/7475* (2013.01); *G09F 19/327* (2013.01); *A61G 7/0506* (2013.01); *A61G 7/05* (2013.01)
USPC ....... 235/462.01; 235/435; 235/439; 235/454

(58) Field of Classification Search
USPC .................................. 235/435, 439, 451, 462
See application file for complete search history.

(56) References Cited

U.S. PATENT DOCUMENTS

| | | | |
|---|---|---|---|
| 4,811,435 A | 3/1989 | Foster et al. | |
| 4,850,009 A | 7/1989 | Zook et al. | |
| 4,857,716 A | 8/1989 | Gombrich et al. | |
| 5,640,953 A | 6/1997 | Bishop et al. | |
| 5,771,511 A * | 6/1998 | Kummer et al. | .................. 5/600 |
| 5,914,701 A | 6/1999 | Gersheneld et al. | |
| 6,171,264 B1 | 1/2001 | Bader | |
| 6,190,326 B1 | 2/2001 | McKinnon et al. | |

(Continued)

FOREIGN PATENT DOCUMENTS

| | | |
|---|---|---|
| WO | WO 00/03344 | 1/2000 |
| WO | WO 01/86575 | 11/2001 |
| WO | WO 2004/095179 | 11/2004 |
| WO | WO 2006/065563 | 6/2006 |

OTHER PUBLICATIONS

European Search Report for EP 12181304.2, dated Dec. 14, 2012.

*Primary Examiner* — Michael G Lee
*Assistant Examiner* — Matthew Mikels
(74) *Attorney, Agent, or Firm* — Barnes & Thornburg LLP

(57) ABSTRACT

A patient support apparatus includes a patient support, a multi-directional optical reader, and a control system. The multi-directional optical reader is secured to the patient support and configured to detect a first indicia having a predetermined pattern. The control system includes a processor in communication with the multi-directional optical reader, a transmitter in communication with the processor, and a memory in communication with the processor. The memory stores an identifier associated with the patient support apparatus. The processor receives a signal from the multi-directional optical reader indicative of data from the first indicia detected by the multi-directional optical detector. In response to receiving the signal, the processor performs a set of instructions. The set of instructions performed by the processor include (i) linking the data from the first indicia with the identifier, and (ii) communicating the linked data from the first indicia and identifier to a network external to the patient support apparatus.

20 Claims, 6 Drawing Sheets

(56) References Cited

U.S. PATENT DOCUMENTS

| | | |
|---|---|---|
| 6,287,252 B1 | 9/2001 | Lugo |
| 6,435,413 B1 * | 8/2002 | Kumagai et al. ......... 235/462.45 |
| 6,478,748 B1 | 11/2002 | Kuhn et al. |
| 6,671,563 B1 | 12/2003 | Engelson et al. |
| 7,480,951 B2 | 1/2009 | Weismiller et al. |
| 7,853,457 B2 | 12/2010 | Klabunde et al. |
| 7,868,740 B2 | 1/2011 | McNeely et al. |
| 2002/0013518 A1 | 1/2002 | West et al. |
| 2002/0044059 A1 | 4/2002 | Reeder et al. |
| 2002/0147390 A1 | 10/2002 | Markis et al. |
| 2004/0059599 A1 | 3/2004 | McIvor |
| 2004/0100361 A1 | 5/2004 | Brackett et al. |
| 2004/0186358 A1 | 9/2004 | Chernow et al. |
| 2005/0043964 A1 | 2/2005 | Thielscher et al. |
| 2005/0101844 A1 | 5/2005 | Duckert et al. |
| 2005/0131733 A1 | 6/2005 | Lubow |
| 2006/0015589 A1 | 1/2006 | Ang et al. |
| 2010/0306921 A1 | 12/2010 | Kramer |
| 2011/0166891 A1 | 7/2011 | Zerhusen et al. |

\* cited by examiner

MULTI-DIRECTIONAL OPTICAL READER FOR A PATIENT SUPPORT

BACKGROUND

The present disclosure is related to the arrangement and operation of patient support apparatuses with sensors for gathering information from the environment around the patient support. More specifically, the present disclosure is related to a patient support apparatus including a multi-directional optical reader.

Patient support apparatuses, such as hospital beds for example, are used in hospitals, nursing homes, private homes, and the like. In some care environments, the locations of patient supports and other pieces of equipment are tracked by sensors within the care environment. When the locations of patient supports and other pieces of equipment are tracked, administrators can monitor and evaluate the deployment of the patient supports and other pieces equipment.

Patient support apparatuses and other pieces of equipment are known to be fitted with electronic transmitters such as RFID transmitters or reflectors to facilitate tracking of the patient supports and other pieces of equipment. The use of such electronic transmitters requires that various locations around the care environment be equipped with sensors to determine the presence or absence of the patient supports or the other pieces of equipment.

SUMMARY

The present application discloses one or more of the features recited in the appended claims and/or the following features which, alone or in any combination, may comprise patentable subject matter:

A patient support apparatus is disclosed herein. The patient support apparatus may include a patient support, a multi-directional optical reader, and a control system. The multi-directional optical reader may be secured to the patient support and may be configured to detect a first indicia having a predetermined pattern. The control system may include a processor in communication with the multi-directional optical reader, a transmitter in communication with the processor, and a memory in communication with the processor. The memory may store an identifier associated with the patient support apparatus. The processor may receive a signal from the multi-directional optical reader indicative of data from the first indicia detected by the multi-directional optical detector. The processor may also perform a set of instructions in response to the multi-directional optical reader communicating the data from the first indicia. The set of instructions performed by the processor may include (i) linking the data from the first indicia with the identifier, and (ii) communicating the linked data from the first indicia and identifier to a network external to the patient support apparatus.

In some embodiments, the multi-directional optical reader may include a first sensor having a first field of view and a second sensor having a second field of view. The first sensor and the second sensors may be bar code readers. The field of view of the first sensor may be directed toward a head end of the patient support and the field of view of the second sensor may be directed toward a foot end of the patient support. The first field of view and the second field of view may partially overlap.

In some embodiments, the multi-directional optical reader may be secured to a barrier extending at least partially around the patient support. The first sensor may be oriented to detect indicia outside a footprint of the patient support apparatus at a first angle relative to the barrier and the second sensor may be oriented to detect indicia outside of the footprint of the patient support apparatus at a second angle relative to the barrier.

In some embodiments, the first indicia may be coupled to a wall and the multi-directional optical reader may be configured to detect a second indicia coupled to a monitor and to provide a second signal indicative of data from the second indicia coupled to the monitor. It is contemplated that in some embodiments the set of instructions performed by the processor may further include: (iii) linking the data from the second indicia to the identifier, and (iv) transmitting the linked data to the network.

In some embodiments, the patient support may include a user interface with a display and a user input, the user interface in communication with the processor. It is contemplated that the processor may perform a set of instructions in response to the multi-directional optical reader communicating the data from the second indicia. The set of instructions performed by the processor may include (i) communicating a prompt to the display requesting information from the monitor, (ii) receiving a response to the prompt from the user input, (iii) linking the response to the identifier, and (iv) communicating the linked data to a network.

In some embodiments, the multi-directional optical reader may include a first sensor having a first field of view set at a first angle relative to the patient support and a second sensor having a second field of view set at a second angle relative to the patient support. The first field of view may be directed toward a head end of the patient support and the second field of view may be directed toward a foot end of the patient support.

In some embodiments, the first indicia may be coupled to a wall and the multi-directional optical reader may be configured to detect a second indicia coupled to a caregiver identification item. The multi-directional optical reader may also provide a second signal indicative of data from the second indicia coupled to the caregiver identification item and associated with the caregiver. It is contemplated that the set of instructions performed by the processor may further include: (iii) linking the data from the second indicia and the identifier, and (iv) transmitting the linked data to the network. In some embodiments, the patient support may include a user interface with a display and a user input. The user interface may be in communication with the processor. The processor may perform a set of instructions in response to the multi-directional optical reader communicating the data from the second indicia. The set of instructions performed by the processor may include (i) communicating a prompt to the enter information, (ii) receiving a response to the prompt from the user input, (iii) linking the response to the data from the first indicia and the identifier, and (iv) communicating the linked data to a network. In some embodiments, the network includes a hospital information system.

A method of determining a location of a patient support apparatus is also disclosed. The method may include the steps of detecting a first indicia having a predetermined pattern with a multi-directional optical reader secured to the patient support apparatus, linking data from the first indicia with an identifier associated with the patient support apparatus, and communicating the linked data and identifier to a network.

In some embodiments, the method may also include the steps of detecting a second indicia with the multi-directional optical reader, linking data from the second indicia with identifier, and communicating the linked data to the network. It is contemplated that the second indicia may be coupled to and associated with one of a monitor, a caregiver identification item, a patient identification item, and a support surface.

Additional features, which alone or in combination with any other feature(s), including those listed above and those listed in the claims may comprise patentable subject matter and will become apparent to those skilled in the art upon consideration of the following detailed description of illustrative embodiments exemplifying the best mode of carrying out the embodiments as presently perceived.

BRIEF DESCRIPTION OF THE DRAWINGS

The detailed description particularly refers to the accompanying figures in which.

DETAILED DESCRIPTION OF THE DRAWINGS

Figure 1:
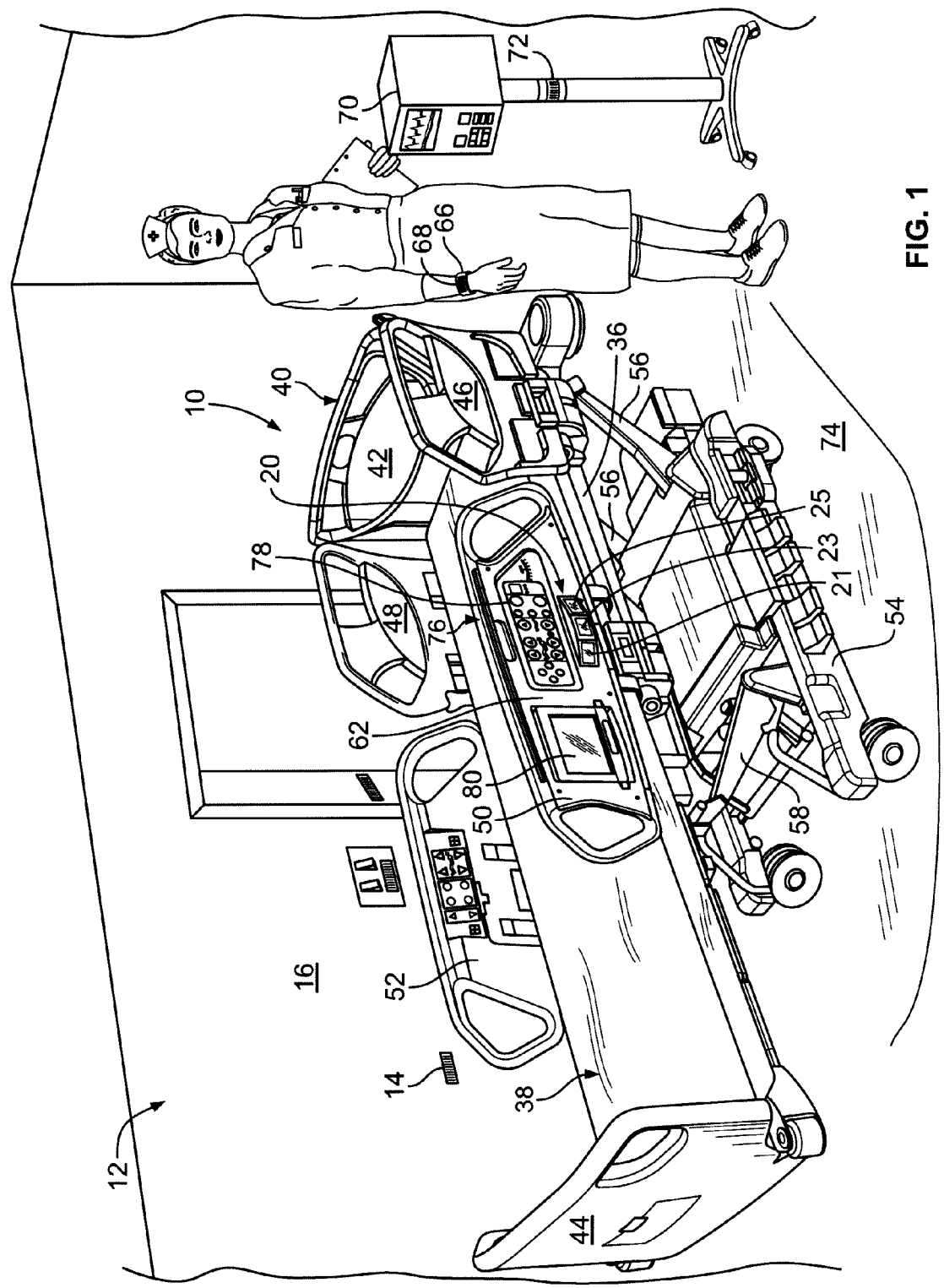
FIG. 1 is a perspective view of a patient support apparatus according to the present disclosure in a room, the patient support apparatus including a multi-directional optical reader coupled to a siderail.

A patient support apparatus shown in FIG. 1 is illustratively embodied as a hospital bed 10 in a patient room 12. The patient room 12 has a predetermined indicia 14 coupled to a wall 16 and associated with the patient room 12 in a hospital information system 32 and in a nurse call system 34. The bed 10 includes a multi-directional optical reader 20 with three sensors 21, 23, 25 and a control system 22. It should be understood that the optical reader 20 may include additional sensors, or fewer sensors, in other embodiments. As shown diagrammatically in FIG. 2, the control system 22 includes a processor 24, a transmitter/receiver 26, and a memory 28 containing a bed identifier 30. The control system 22 is in communication with the reader 20, the hospital information system 32, and the nurse call system 34. The transmitter/receiver 26 is illustratively a wireless RF communication device. In other embodiments, the transmitter/receiver 26 may be only a transmission device or may be separate transmission and receiving devices as known in the art. In some embodiments, transmitter/receiver 26 may be wired.

The multi-directional optical reader 20 cooperates with the control system 22 to communicate data for locating the bed 10 to the hospital information system 32 and the nurse call system 34. For example, when the sensors 21, 23, 25 of the multi-directional optical reader 20 detect the indicia 14, the reader 20 provides a signal indicative of the indicia 14 to the processor 24 of the control system 22. In response to the reader 20, the processor 24 performs a series of steps. First, the processor 24 links the data from the indicia 14 received from the reader 20 with the bed identifier 30 from the memory 28. Then, the processor 24 communicates the linked data from indicia 14 and bed identifier 30 to the hospital information system 32 and/or the nurse call system 34. The data from the indicia 14 is associated with a location in the hospital information system 32 and/or in the nurse call system 34. Thus, the hospital information system 32 and the nurse call system 34 have information linking bed 10 with a location and can track bed location and allocation.

The bed 10 includes an intermediate frame 36 supporting a support surface 38 and barriers 40 extending around the support surface 38 as shown in FIG. 1. The barriers 40 include a headboard 42, a footboard 44, head rails 46, 48, and siderails 50, 52. The headboard 42 and the footboard 44 are removable from the bed 10. The headrails 46, 48 and the siderails 50, 52 may be raised and lowered to allow access to a patient supported on a support surface 38.

The intermediate frame 36 is supported above a base frame 54 by head end lift arms 56 and foot end lift arms 58 as shown in FIG. 1. The lift arms 56, 58 are movable to change the height or angle of the intermediate frame 36 relative to the base frame 54. The lift arms 56, 58 are moved by patient support drives 60, shown diagrammatically in FIG. 2. The patient support drives 60 are in communication with the processor 24 of control system 22.

In the embodiment of FIG. 1, the multi-directional optical reader 20 is coupled to an exterior surface 62 of the siderail 50 as shown. The sensors 21, 23, 25 of the reader 20 have different fields of view relative to the siderail 50 so as to detect the indicia 14 when the indicia 14 is in various orientations relative to the siderail 50. In the illustrative embodiment, the sensor 21 has a field of view directed toward the foot end of the bed 10, the sensor 23 has a field of view directed outwardly from the bed 10 and substantially perpendicular to the siderail 50, and the sensor 25 has a field of view directed toward the head end of the bed 10. The field of view of the sensor 21 partially overlaps the field of view of the sensor 23 and the field of view of the sensor 23 partially overlaps the field of view of the sensor 25. The sensors 21, 23, 25 are illustratively bar code scanners for detecting linear bar codes. In other embodiments, the sensors 21, 23, may be other optical detectors for detecting other linear codes, bulls eye codes, concentric circle codes, starburst pattern codes, color patterns, lights, or other optically detectable indicia. In other embodiments, the reader 20 may include sensors distributed around the bed 10, may be coupled to any of the barriers 40, or may be coupled to another structure of the bed 10.

Figure 2:
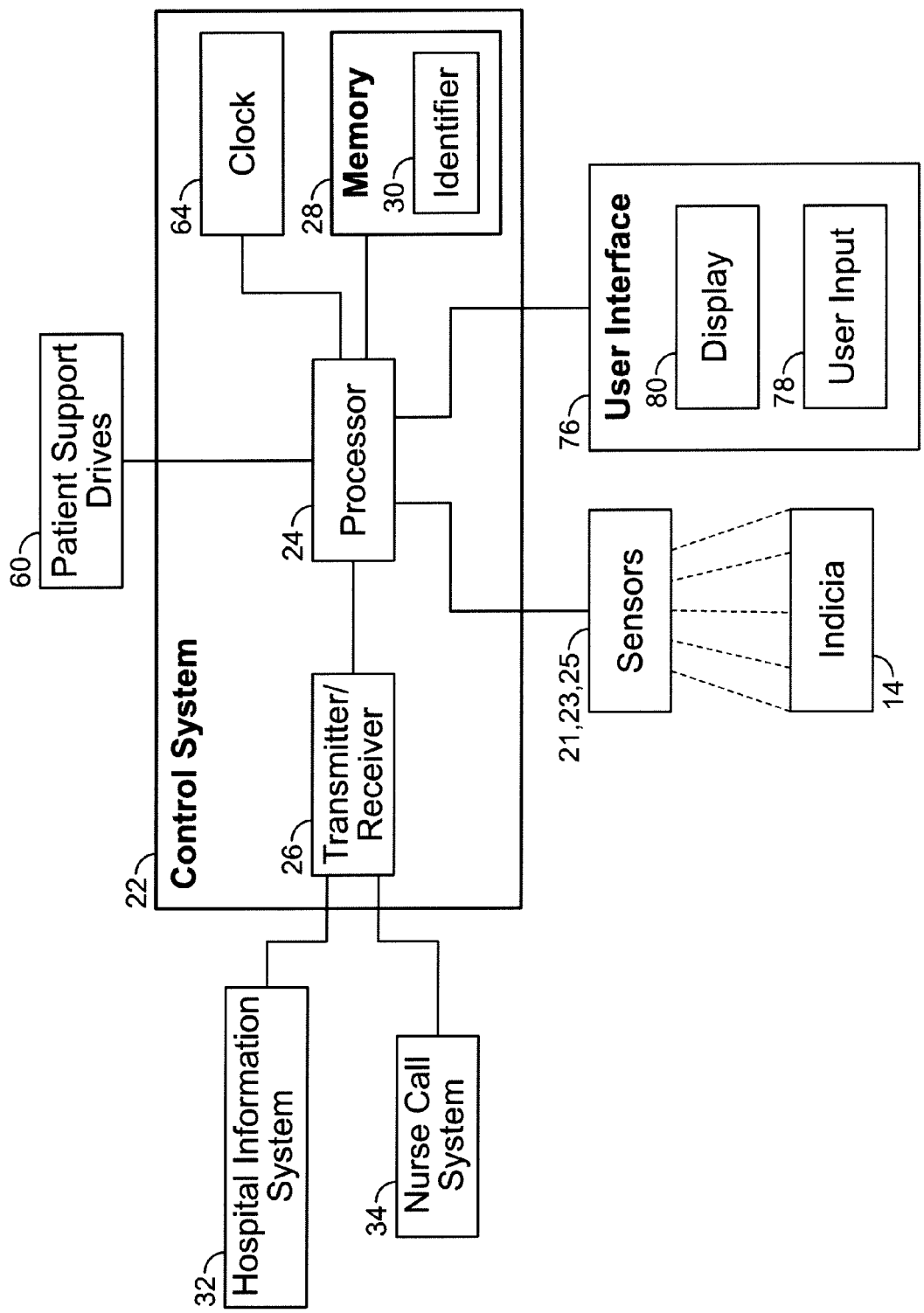
FIG. 2 is a diagrammatic representation of a control system of the patient support apparatus of FIG. 1 along with components in communication with the control system.

The control system 22 also includes a real-time clock 64 communicating a time stamp to the processor 24 so that the location of the bed 10 can be tracked over time as shown in FIG. 2. Illustratively, the time stamp includes a time and a date. In other embodiments, the time stamp may include only a time or only a date. In response to the reader 20 communicating data from the indicia 14 on the wall 16, the processor 24 of the control system 22 performs the step of linking the time stamp from clock 64, the data from indicia 14, and the bed identifier 30 from memory 28. Then, the processor 24 communicates the linked time stamp, data from the indicia 14, and the bed identifier 30 to the hospital information system 32 and/or the nurse call system 34. The hospital information system 32 and/or the nurse call system 34 then associate the data from the indicia 14 with a location. Thus, the hospital information system 32 and the nurse call system 34 have information relating the bed 10 to a location at various points over time.

A caregiver 69 wearing a bracelet 66 with a predetermined indicia 68 printed thereon, as suggested in FIG. 1, may be linked with the bed 10 from time tot time indicating the caregiver's presence at the bed 10. The indicia 68 may be associated with a particular caregiver 69, or with a class of caregivers. In other embodiments, the caregiver carries an ID badge with indicia printed thereon, a clipboard with indicia printed thereon, or some other object with indicia coupled thereto. In the illustrated embodiment, the indicia 68 is associated in the hospital information system 32 and in the nurse call system 34 with the caregiver's employee number. In other embodiments, the indicia 68 on the bracelet 66 may be associated with a caregiver's name, title, skill set, or other caregiver information. The multi-directional optical reader 20 is configured to communicate data from the indicia 68 to the processor 24. In response to the reader 20 communicating data from the indicia 14 on the wall 16 and data from the indicia 68 on the bracelet 66, the processor 24 of the control system 22 performs the step of linking the data from the indicia 68, the time stamp from clock 64, the data from the indicia 14, and the bed identifier 30 received from the memory 28. Then, the processor 24 communicates the linked data from the indicia 68, time stamp, data from indicia 14, and bed identifier 30 to the hospital information system 32 and/or the nurse call system 34. The hospital information system 32 and/or the nurse call system 34 then associate the data from the indicia 14 with a location and the data from the indicia 68 with the caregiver's employee number. Thus, the hospital information system 32 and the nurse call system 34 have information for relating the caregiver's presence to the location of the bed 10 at various points over time.

A patient (not shown) is linked with the bed 10 from time to time indicated the patient's presence at the bed 10. A patient indicia (not shown) is associated with a patient name or other information in the hospital information system 32 and/or in the nurse call system 34. The patient indicia may be printed on a bracelet, an ID badge, or may be coupled to another object. When the patient indicia is detected by the reader 20, the reader 20 is configured to communicate data regarding the patient indicia to the processor 24. In response to reader 20 communicating data from indicia 14 on wall 16 and from the patient indicia, the processor 24 of the control system 22 performs the step of linking the data from the patient indicia, the time stamp from clock 64, the data from indicia 14, and the bed identifier 30 received from memory 28. Then, processor 24 communicates the linked data from the patient indicia, time stamp, data from indicia 14, and bed identifier 30 to the hospital information system 32 and/or the nurse call system 34. The hospital information system 32 and/or the nurse call system 34 then associate the data from indicia 14 with a location and the patient data with a patient name. Thus, the hospital information system 32 and the nurse call system 34 have information relating the patient's presence to the location of the bed 10 at various points over time. In some embodiments, the patient is associated with a particular bed in the hospital information system 32 and/or nurse call system 34.

The room 12 further contains a heart rate monitor 70 with a predetermined indicia 72 coupled thereto, as shown in FIG. 1, so that the location of the monitor 70 can be linked from time to time to the bed 10. Illustratively, the indicia 72 of the monitor 70 is spaced the same distance from a floor 74 as the indicia 14 on the wall 16 is spaced from the floor 74. The indicia 72 is associated with a monitor identification number in the hospital information system 32 and/or in the nurse call system 34. In other embodiments, the indicia 72 is associated with a monitor serial number, model number, asset tracking number, or some other piece of monitor information. When the reader 20 detects indicia 72, the reader 20 is configured to communicate data from the indicia 72 to the processor 24. In response to reader 20 communicating data from the indicia 14 on the wall 16 and data from the indicia 72 on the monitor 70, the processor 24 of the control system 22 performs the step of linking data from the indicia 72, the time stamp from clock 64, the data from the indicia 14, and the bed identifier 30 received from memory 28. Then, processor 24 communicates the linked data from the indicia 72, time stamp, data from the indicia 14, and bed identifier 30 to the hospital information system 32 and/or the nurse call system 34. The hospital information system 32 and the nurse call system 34 then associate the data from indicia 72 with a monitor identification number and the data from the indicia 14 with a location. Thus, the hospital information system 32 and the nurse call system 34 have information relating the monitor's presence to the location of the bed 10 at various points over time. In other embodiments, indicia may be applied to other movable hospital equipment such as IV pumps, patient lifts, sequential compression devices, and the like. Such equipment may also be tracked around a hospital by indicia applied to the equipment in a fashion similar to that of the monitor 70.

The siderail 50 includes a user interface 76 including a user input 78, illustratively a plurality of buttons, and a display 80 as shown, for example, in FIG. 1. In some embodiments, the display 80 may be a touch sensitive LCD and may provide additional user inputs as suggested in FIGS. 7-8. The user interface 76 is in communication with the processor 24 of the control system 22 so that inputs from the user input 78 are received by the processor 24 and screens sent from the processor 24 are shown on the display 80. Additionally, the user input 78 is operable to direct the patient support drives 60 through the control system 22 to position the bed 10 so that the reader 20 is spaced the same distance as the indicia 14, 72 from the floor 74. In some embodiments, the user input 78 may be operable to associate a patient with the bed 10 in response to a caregiver entering a patient identifier into the user input 78.

Figure 7:
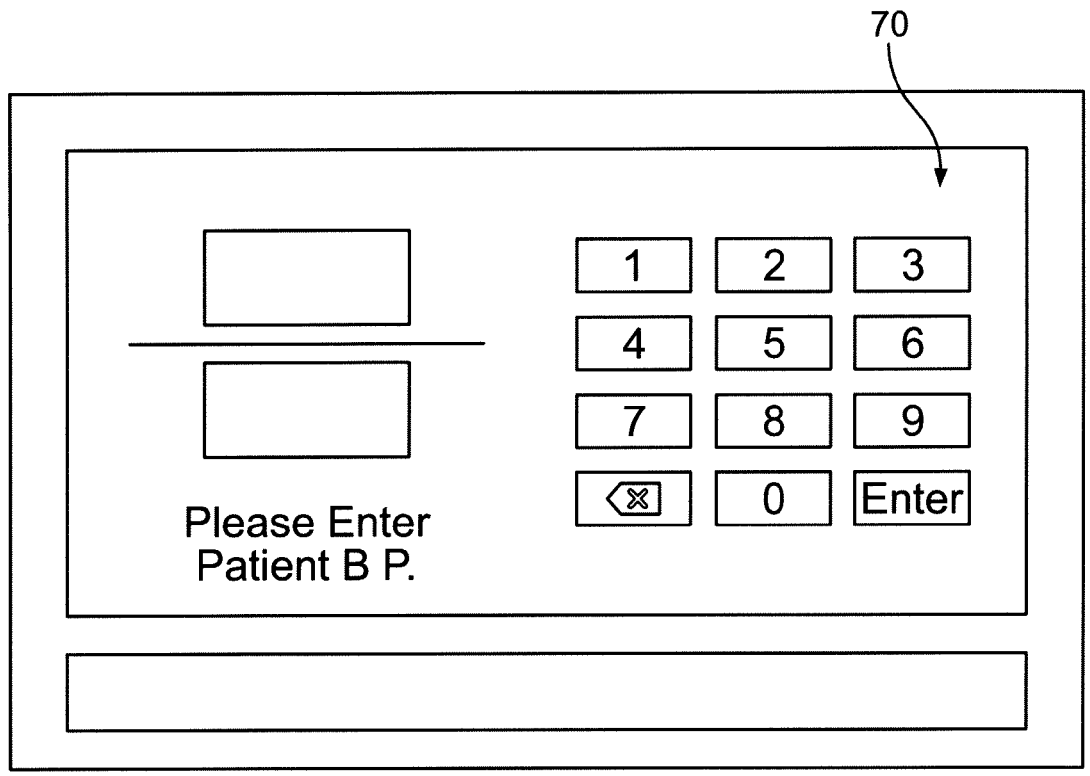
FIG. 7 is a front elevation view of a screen displaying a request for a patient blood pressure reading to be entered by a caregiver.

The user interface 76 is operable to receive patient information from a caregiver so that the patient information is stored in the hospital information system 32 and the nurse call system 34 as suggested by FIG. 7. For example, in response to the reader 20 communicating data from the indicia 14 on the wall 16 and from the indicia 68 on the caregiver bracelet 66, the processor 24 of the control system 22 performs the step of creating a prompt on the display 80 requesting patient information from the caregiver. A first example prompt requesting patient blood pressure is shown in FIG. 7. In response to a caregiver inputting the requested patient information via the user interface 76, the processor 24 links the patient information received from the user interface 76, the data from indicia 68 on the bracelet 66, the time stamp from clock 64, the data from the indicia 14 on the wall 16, and bed identifier 30 received from memory 28. Then, processor 24 communicates the linked information to the hospital information system 32 and/or the nurse call system 34. The hospital information system 32 and/or the nurse call system 34 then associate the data from the indicia 68 with a caregiver's employee number and the data from the indicia 14 with a location. Thus, the hospital information system 32 and the nurse call system 34 can add the linked information to a patient file.

Figure 8:
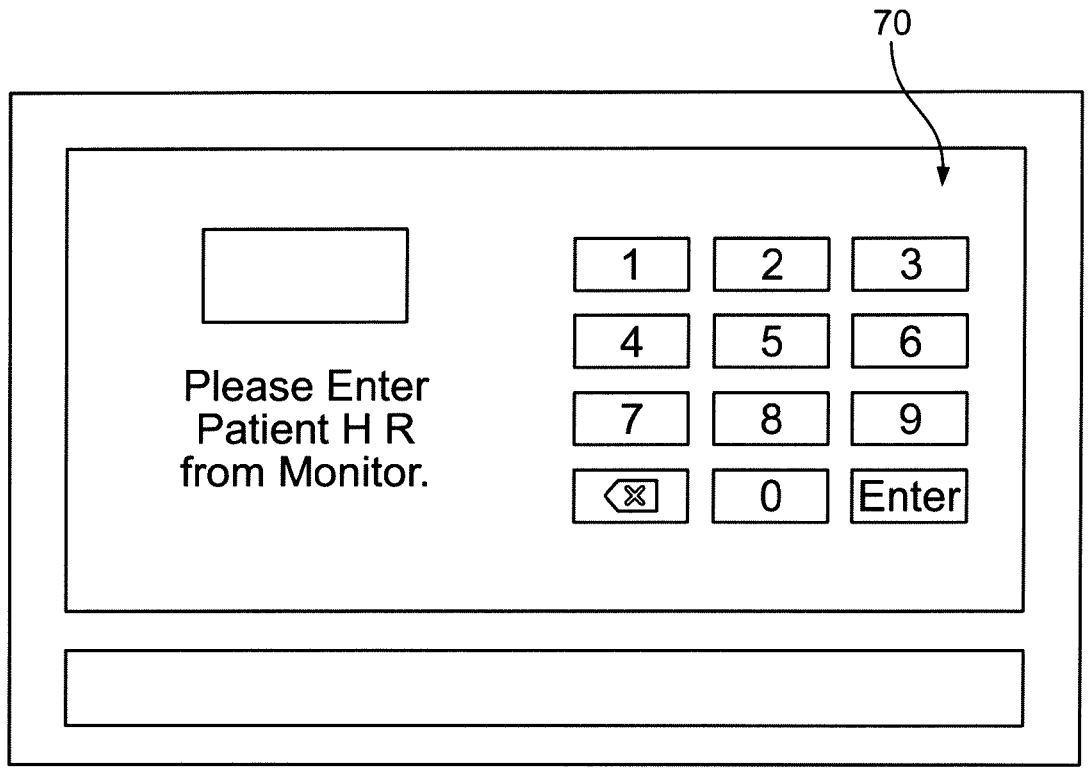
FIG. 8 is a front elevation view of a screen displaying a request for a patient heart rate to be entered by a caregiver.

The user interface 76 is also operable to prompt a caregiver 69 to enter patient information from the monitor 70 input. For example, in response to reader 20 communicating data from the indicia 14 on the wall 16, data from the indicia 72 on monitor 70, and data from the indicia 68 on the caregiver bracelet 66, the processor 24 of the control system 22 performs the step of creating a prompt on the display 80 requesting that the caregiver 69 input patient information from the monitor 70. A second example prompt requesting a patient heart rate from the monitor 70 is shown in FIG. 8. In response to a caregiver inputting the requested patient information via the user interface 76, the processor 24 links the patient information received from the user interface 76, the data from the indicia 72 on the monitor 70, the data from the indicia 68 on the bracelet 66, the time stamp from clock 64, the data from the indicia 14 on the wall 16, and bed identifier 30 received from memory 28. Then, processor 24 communicates the linked information to the hospital information system 32 and/or the nurse call system 34. The hospital information system 32 and/or the nurse call system 34 then associate the data with a monitor identification number, a caregiver's employee number, and a location. Thus, the hospital information system 32 and the nurse call system 34 can add the linked information to a patient file.

Figure 3:
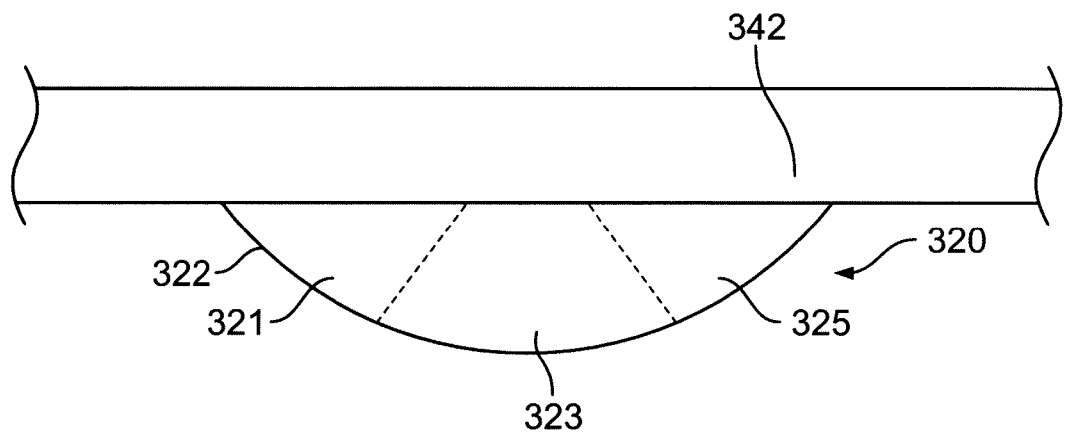
FIG. 3 is a top plan view of a first embodiment of a multi-directional optical reader, the multi-directional optical reader coupled to a headboard.

FIG. 3 shows another embodiment of a multi-directional optical reader 320 that is operationally similar to the multi-directional optical reader 20 and is operable with the control system 22 of the bed 10 as described above. The reader 320 is coupled to an exterior surface 362 of a headboard 342 and includes a plurality of sensors 321, 323, 325. The sensors 321, 323, 325 of the reader 320 have different fields of view relative to the headboard 342 so as to detect indicia at different orientations relative to the headboard 342. The sensors 321, 323, 325 of the reader 320 form an arcuate front face 322. The sensors 321, 323, 325 are illustratively bar code scanners for detecting linear bar codes. In other embodiments, the sensors 321, 323, 325 may be other optical detectors for detecting other linear codes, bulls eye codes, concentric circle codes, starburst pattern codes, color patterns, lights, or other optically detectable indicia.

Figure 4:
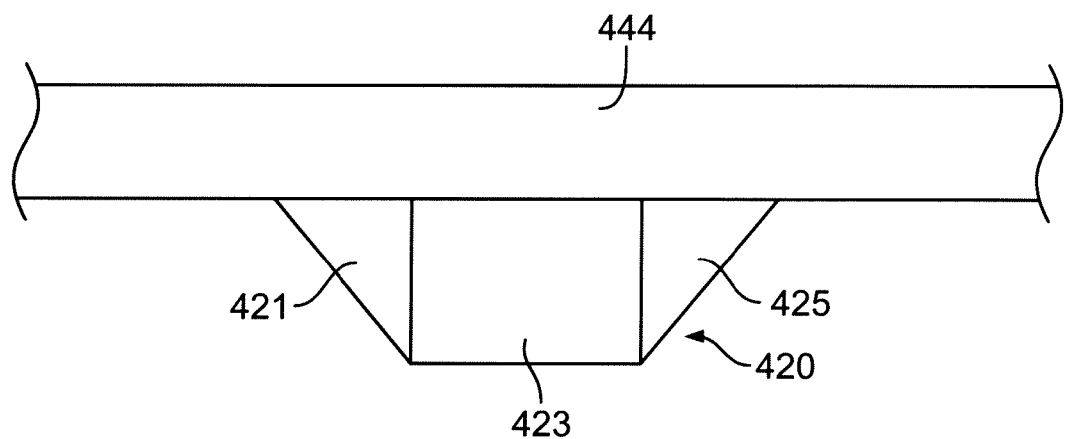
FIG. 4 is a top plan view of a second embodiment of a multi-directional optical reader, the multi-directional optical reader coupled to a footboard.

FIG. 4 shows yet another embodiment of a multi-directional optical reader 420 that is operationally similar to the multi-directional optical reader 20 and is operable with the control system 22 of the bed 10 as described above. The reader 420 is coupled to an exterior surface 462 of a footboard 444 and includes a plurality of sensors 421, 423, 425. The sensors 421, 423, 425 of the reader 420 have different fields of view relative to the footboard 444 so as to detect indicia at different orientations relative to the footboard 444. The sensors 421, 423, 425 are illustratively bar code scanners for detecting linear bar codes. In other embodiments, the sensors 421, 423, 425 may be other optical detectors for detecting other linear codes, bulls eye codes, concentric circle codes, starburst pattern codes, color patterns, lights, or other optically detectable indicia.

Figure 5:
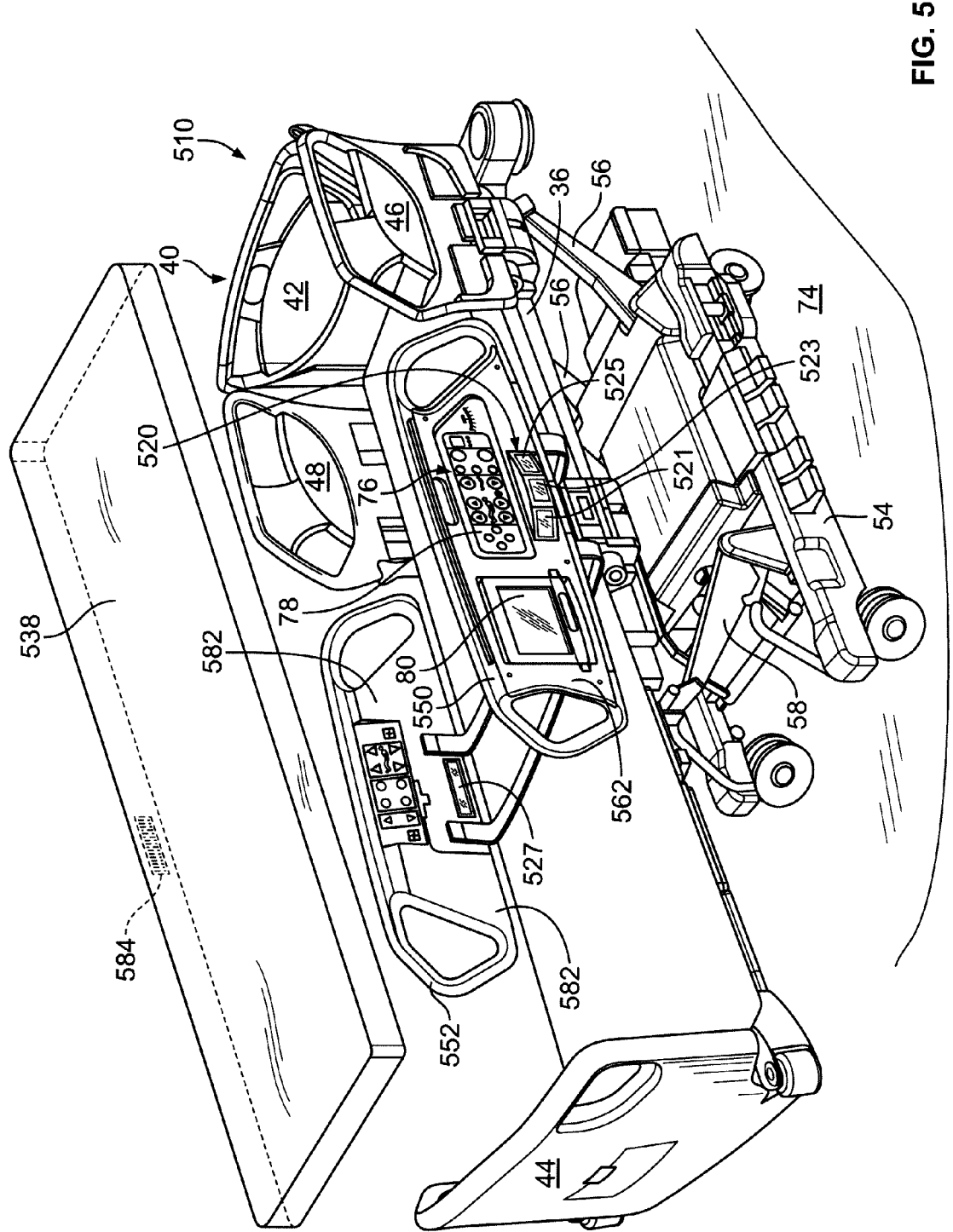
FIG. 5 is a perspective view of an alternative patient support apparatus of the present disclosure, the patient support apparatus including a first optical reader coupled to an exterior surface of a siderail and a second optical reader coupled to an interior surface of a siderail.

FIG. 5 shows another embodiment of a bed 510. The bed 510 is similar to the bed 10 and like features are denoted with like reference numbers. The bed 510 includes a multi-directional optical detector 520 having a plurality of sensors 521, 523, 525, 527. The reader 520 is configured for use with the control system 22 described above.

The sensors 521, 523, 525 of the reader 520 are coupled to an exterior surface 562 of a first siderail 550 and are operationally similar to the sensors 21, 23, 25 of the bed 10. The sensor 527 is coupled to an interior surface 582 of a second siderail 552. The sensors 521, 523, 525, 527 are illustratively bar code scanners for detecting linear bar codes as suggested by an indicia 584 in FIG. 5. In other embodiments, the sensors 521, 523, 525, 527 may be other optical detectors for detecting other linear codes, bulls eye codes, concentric circle codes, starburst pattern codes, color patterns, lights, or other optically detectable indicia.

The bed 510 also includes a support surface 538 with a predetermined indicia 584 applied to a side 586 of support surface 538 as shown, for example in FIG. 5. The indicia 584 is positioned so as to be displayed for detection by sensor 527 when the support surface 538 is supported on the bed 10 as suggested in FIG. 5. The indicia 584 is associated with a support surface serial number in the hospital information system 32 and/or in the nurse call system 34. In other embodiments, the indicia 584 is associated with other support surface information such as model number, available support surface functions, support surface manufacture date, or other information. In response to reader 520 communicating a signal indicative of the indicia 584 on the support surface 538, the processor 24 of the control system 22 performs the step of linking data from the indicia 584 on the support surfaces 38 with the bed identifier 30 received from memory 28. Then, processor 24 communicates the linked data from the indicia 584 on the support surface 538 and bed identifier 30 to the hospital information system 32 and/or the nurse call system 34. Additionally, when reader 520 has communicated data from an indicia associated with location, the processor 24 links the data associated with location with the data from the indicia 584 and communicates the linked information to the hospital information system 32 and the nurse call system 34. The hospital information system 32 and the nurse call system 34 then associate the data from the indicia 584 with a support surface serial number. Thus, hospital information system 32 and nurse call system 34 have information relating the support surface's 538 presence to the location of the bed 510 at various points over time.

Figure 6:
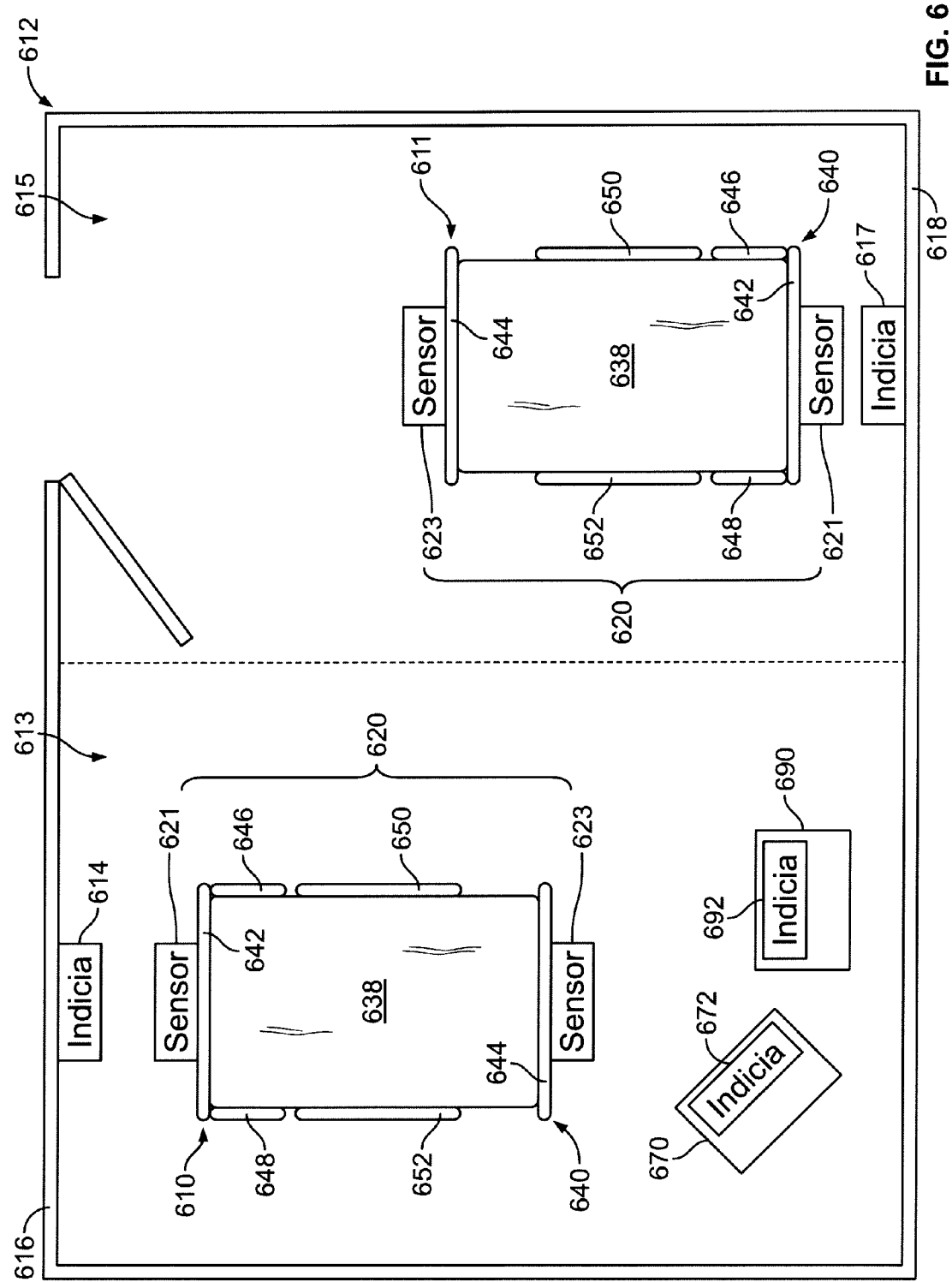
FIG. 6 is a top plan view of a room including a first patient support apparatus and a second patient support apparatus.

In some embodiments, a single room can include multiple locations to be associated with beds, caregivers, patients, and monitors. For example, FIG. 6 shows a pair of beds 610, 611 in a room 612. Room 612 has a first zone 613 with a predetermined indicia 614 coupled to a first wall 616 and a second zone 615 with a predetermined indicia 617 coupled to a second wall 618. The indicia 614 is associated with a first location and the indicia 616 is associated with a second location in the hospital information system 32 and/or in the nurse call system 34. Thus, more than one location is indicated in a single room. Such an arrangement may be advantageous in a critical care unit, multi-patient rooms, or other rooms that accommodate more than one patient support apparatus.

The beds 610, 611 are substantially similar and like components are numbered with like reference numbers in FIG. 6. The beds 610, 611 each include a multi-directional optical reader 620 having a head end sensor 621 and a foot end sensor 623, as shown diagrammatically in FIG. 6. The head end sensor 621 and the foot end sensor 623 are illustratively bar code scanners for detecting linear bar codes. In other embodiments, the head end sensor 621 and the foot end sensor 623 may be other optical detectors for detecting other linear codes, bulls eye codes, concentric circle codes, starburst pattern codes, color patterns, lights, or other optically detectable indicia. The reader 620 is operationally similar to the reader 20 described above and is configured to operate with the control system 22 shown diagrammatically in FIG. 2 as described above.

The beds 610, 611 each include a support surface 638 and barriers 640 extending around support surface 638 as shown in FIG. 6. The barriers 640 include a headboard 642, a footboard 644, a pair of head rails 646, 648 and a pair of siderails 650, 652. In the exemplary embodiment of FIG. 6, the head end sensors 621 of the beds 610, 611 are coupled to the headboard 642. The foot end sensors 623 of the beds 610, 611 are coupled to the footboard 644.

While the head end sensor 621 of the beds 610, 611 is detecting indicia 614, 617 associated with location, the foot end sensor 623 is free to detect other indicia as suggested by FIG. 6. Illustratively, the room 612 further contains patient health monitors 670, 690 with predetermined indicia 672, 692 coupled thereto, respectively. The indicia 672, 692 are associated with monitor identification numbers in the hospital information system 32 and in the nurse call system 34. The foot end sensor 623 may detect the indicia 672, 692 while the head end sensor 621 detects the indicia 614, 617.

Although certain illustrative embodiments have been described in detail above, variations and modifications exist within the scope and spirit of this disclosure as described and as defined in the following claims.

The invention claimed is:

1. A patient support apparatus comprising
a patient support,
a multi-directional optical reader secured to the patient support and configured to detect a first indicia without input from a user, the first indicia having a predetermined pattern, the predetermined pattern including information associated with a location of the first indicia, and
a control system including a processor in communication with the multi-directional optical reader, a transmitter in communication with the processor, and a memory in communication with the processor, the memory storing an identifier associated with the patient support apparatus,
wherein the processor receives a signal from the multi-directional optical reader indicative of data from the first indicia detected by the multi-directional optical detector and performs a set of instructions automatically in response to the multi-directional optical reader communicating the data from the first indicia, the set of instructions performed by the processor including (i) linking the data from the first indicia with the identifier, and (ii) communicating the linked data from the first indicia and identifier to a network external to the patient support apparatus, the network associating the linked data from the first indicia and identifier with a location in the network so as to determine the location of the patient support apparatus.

2. The patient support apparatus of claim 1, wherein the multi-directional optical reader includes a first sensor having a first field of view and a second sensor having a second field of view.

3. The patient support apparatus of claim 2, wherein the first sensor and the second sensors are bar code readers.

4. The patient support apparatus of claim 2, wherein the field of view of the first sensor is directed toward a head end of the patient support.

5. The patient support apparatus of claim 4, wherein the field of view of the second sensor is directed toward a foot end of the patient support.

6. The patient support apparatus of claim 2, wherein the first field of view and the second field of view partially overlap.

7. The patient support apparatus of claim 2, wherein the multi-directional optical reader is secured to a barrier extending at least partially around the patient support and the first sensor is oriented to detect indicia outside a footprint of the patient support apparatus at a first angle relative to the barrier and the second sensor is oriented to detect indicia outside of the footprint of the patient support apparatus at a second angle relative to the barrier.

8. The patient support apparatus of claim 1, wherein the first indicia is coupled to a wall and the multi-directional optical reader is configured to detect a second indicia coupled to a monitor and to provide a second signal indicative of data from the second indicia coupled to the monitor.

9. The patient support apparatus of claim 8, wherein the set of instructions performed by the processor further includes: (iii) linking the data from the second indicia to the identifier, and (iv) transmitting the linked data to the network.

10. The patient support apparatus of claim 8, wherein the patient support includes a user interface with a display and a user input, the user interface in communication with the processor.

11. The patient support apparatus of claim 10, wherein the processor performs a set of instructions in response to the multi-directional optical reader communicating the data from the second indicia, the set of instructions performed by the processor including (i) communicating a prompt to the display requesting information from the monitor, (ii) receiving a response to the prompt from the user input, (iii) linking the response to the identifier, and (iv) communicating the linked data to a network.

12. The patient support apparatus of claim 8, wherein the multi-directional optical reader includes a first sensor having a first field of view set at a first angle relative to the patient support and a second sensor having a second field of view set at a second angle relative to the patient support.

13. The patient support apparatus of claim 12, wherein the first field of view is directed toward a head end of the patient support and the second field of view is directed toward a foot end of the patient support.

14. The patient support apparatus of claim 1, wherein the first indicia is coupled to a wall and the multi-directional optical reader is configured to detect a second indicia coupled to a caregiver identification item and to provide a second signal indicative of data from the second indicia coupled to the caregiver identification item and associated with the caregiver.

15. The patient support apparatus of claim 14, wherein the set of instructions performed by the processor further includes: (iii) linking the data from the second indicia and the identifier, and (iv) transmitting the linked data to the network.

16. The patient support apparatus of claim 14, wherein the patient support includes a user interface with a display and a user input, the user interface in communication with the processor, the processor performing a set of instructions in response to the multi-directional optical reader communicating the data from the second indicia, the set of instructions performed by the processor including (i) communicating a prompt to the enter information, (ii) receiving a response to the prompt from the user input, (iii) linking the response to the data from the first indicia and the identifier, and (iv) communicating the linked data to a network.

17. The patient support apparatus of claim 9, wherein the network includes a hospital information system.

18. A method of determining a location of a patient support apparatus comprising the steps of
detecting, without input from a user, a first indicia having a predetermined pattern with a multi-directional optical reader secured to the patient support apparatus, the first indicia having a predetermined pattern including information associated with a location of the first indicia,
linking data from the first indicia with an identifier associated with the patient support apparatus, and communicating the linked data and identifier to a network automatically, the network associating the linked data from the first indicia and identifier with a location in the network so as to determine the location of the patient support apparatus.

19. The method of claim 18, further comprising the steps of detecting a second indicia with the multi-directional optical reader, linking data from the second indicia with identifier, and communicating the linked data to the network.

20. The method of claim 19, wherein the second indicia is coupled to and associated with one of a monitor, a caregiver identification item, a patient identification item, and a support surface.

\* \* \* \* \*